United States Patent
Bakula et al.

[11] Patent Number: 6,093,197
[45] Date of Patent: Jul. 25, 2000

[54] SPIRAL NERVE CUFF ELECTRODE IMPLANTATION TOOL

[75] Inventors: Tomislav Bakula, Willow Creek; J. Thomas Mortimer, Chagrin Falls, both of Ohio

[73] Assignee: Axon Engineering, Inc., Garfield Heights, Ohio

[21] Appl. No.: 08/986,943

[22] Filed: Dec. 8, 1997

[51] Int. Cl.[7] .................................................. A61B 17/00
[52] U.S. Cl. ............................... 606/129; 606/1; 294/64.1
[58] Field of Search ................. 606/129, 1; 607/118; 294/64.1

[56] References Cited

U.S. PATENT DOCUMENTS

| | | |
|---|---|---|
| 3,859,992 | 1/1975 | Amstutz . |
| 5,542,726 | 8/1996 | Ozawa ..................................... 294/64.1 |
| 5,689,877 | 11/1997 | Grill, Jr. et al. . |
| 5,746,462 | 5/1998 | Lee et al. ................................ 294/64.1 |

FOREIGN PATENT DOCUMENTS

| | | |
|---|---|---|
| WO 93/24058 | 12/1993 | WIPO . |
| WO 96/41570 | 12/1996 | WIPO . |

*Primary Examiner*—Michael H. Thaler
*Attorney, Agent, or Firm*—Jerrold J. Litzinger

[57] ABSTRACT

A tool for implanting spiral nerve cuff electrodes about a nerve which can be maneuvered into difficult-to-access areas within the body of a mammal. The tool consists of a handle/control device which is coupled to an electrode holding valve assembly at the distal end of the tool by a flexible connection, allowing for accurate positioning of the electrode at the implantation site. The tool handle/control device is coupled to the valve assembly such that the control device can be rotated to release the electrode, which is held to the valve assembly by a vacuum, while the handle is held steady to ensure the precise location of the electrode at a site remote from the handle. The vacuum holding the electrode can be removed from portions of the electrode sequentially, allowing the spiral electrode to curl around the nerve.

16 Claims, 3 Drawing Sheets

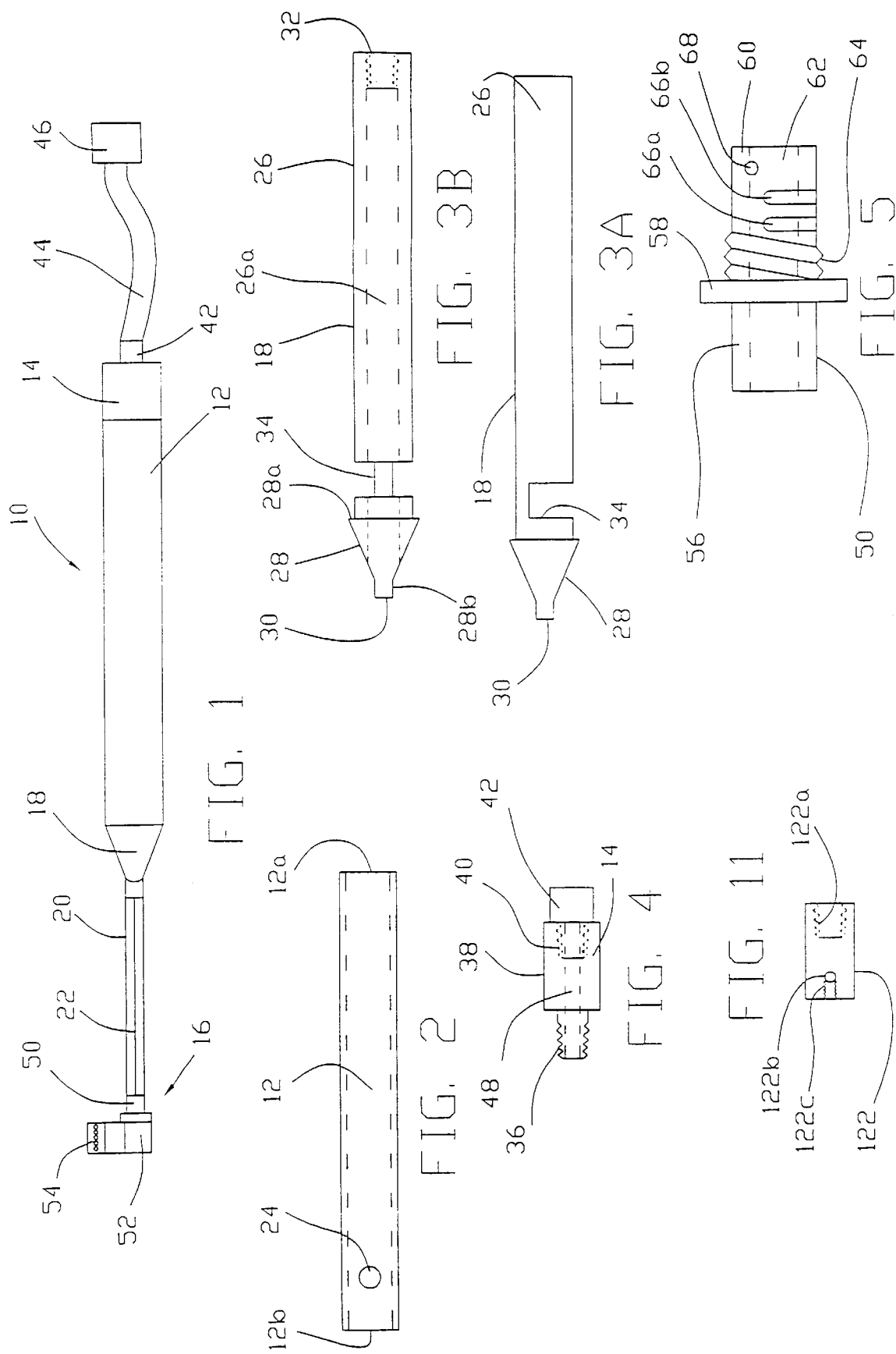

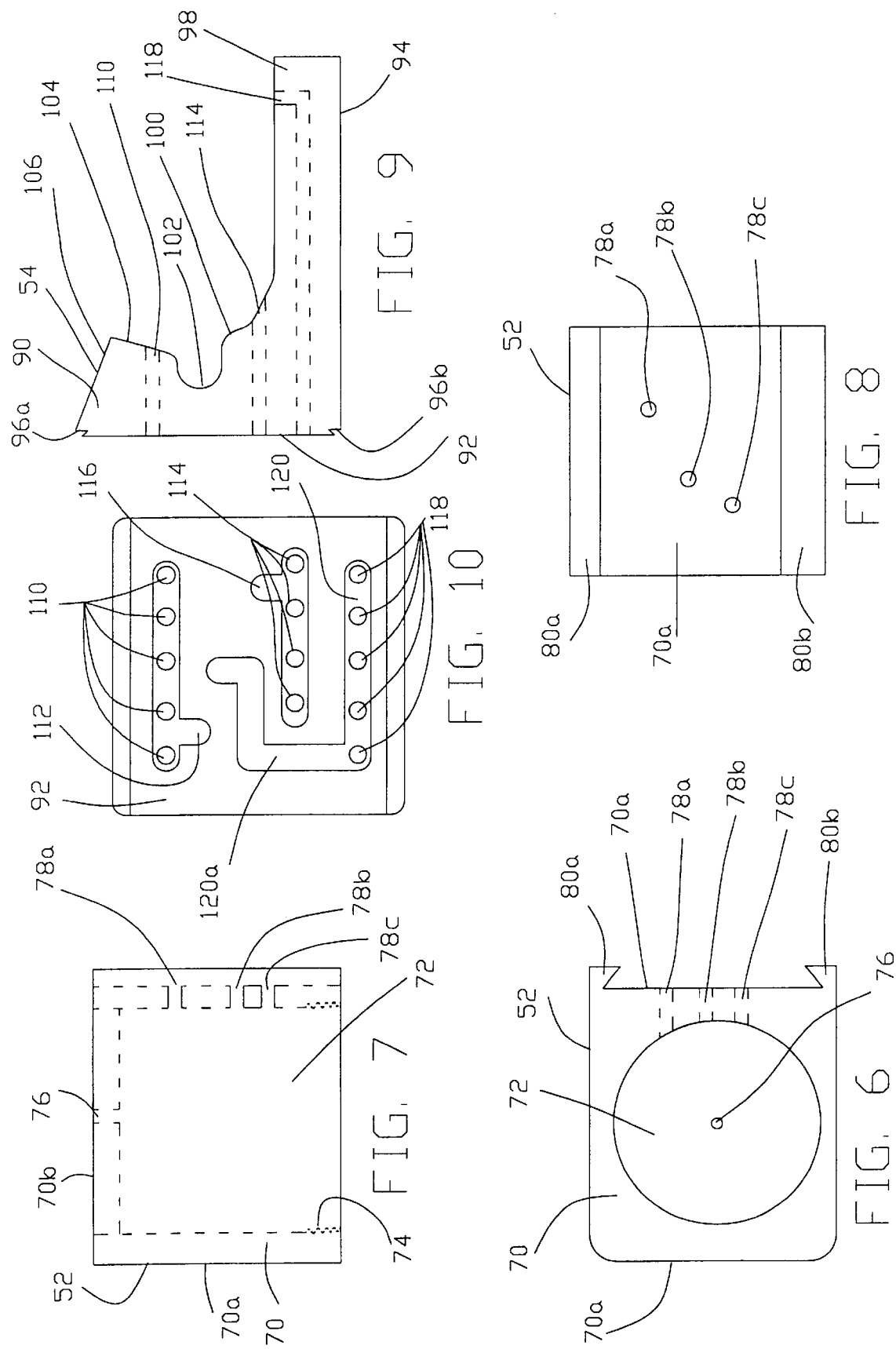

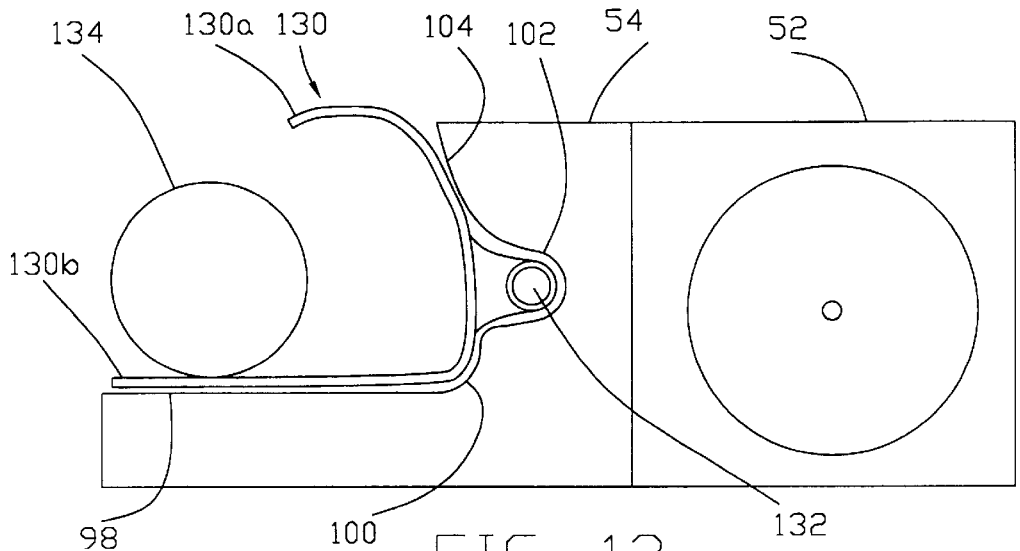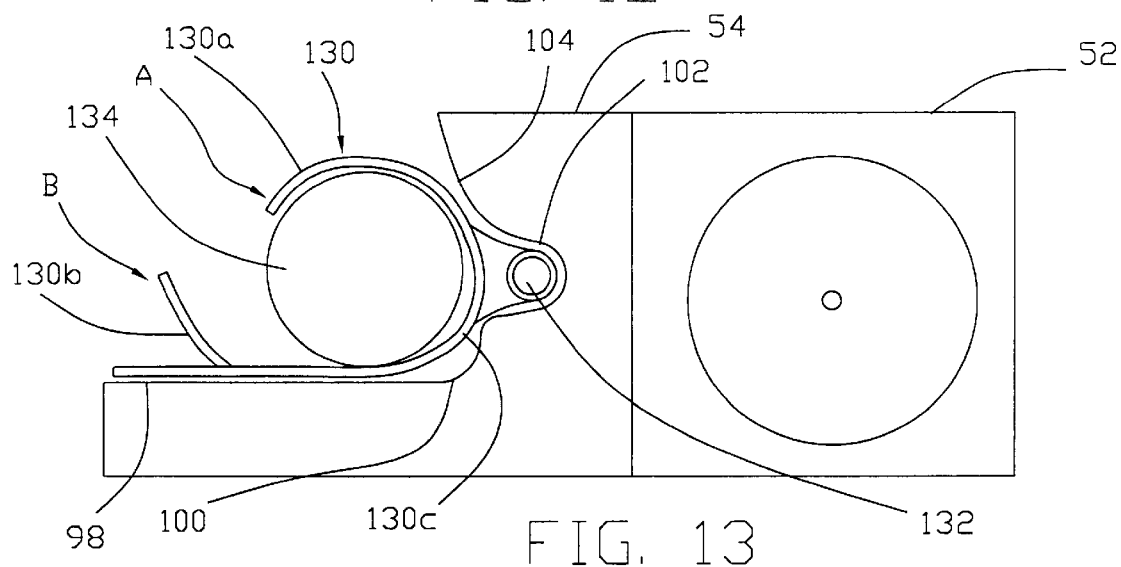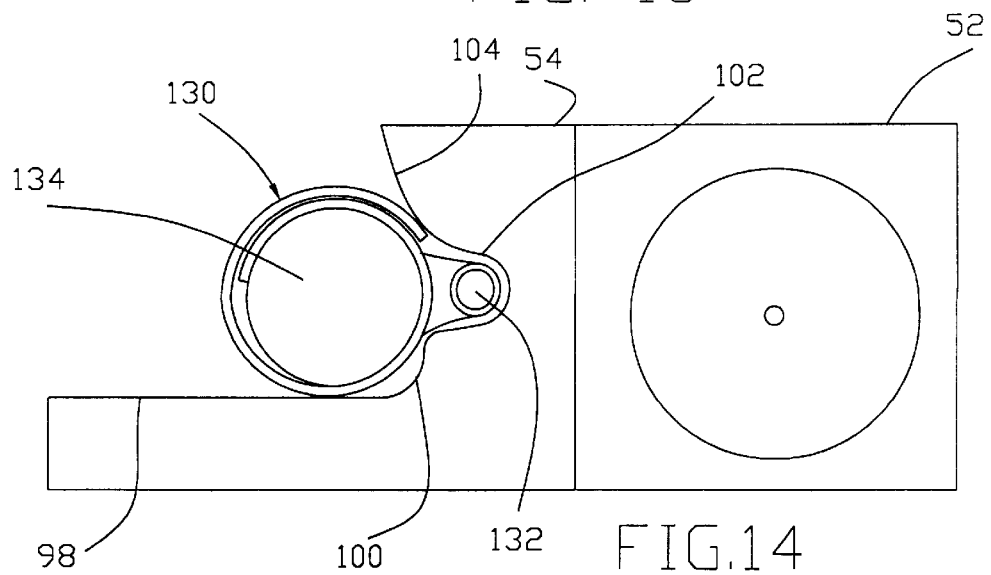

SPIRAL NERVE CUFF ELECTRODE IMPLANTATION TOOL

BACKGROUND OF THE INVENTION

1. Field of the Invention

The present invention relates generally to a medical instrument, and, in particular, to a device for implanting spiral cuff electrodes about the trunk of a nerve for the introduction of electrical signals.

2. Description of the Related Art

The use of electrodes to stimulate nerves and other body tissues has been well known for many years. More specifically, the use of nerve cuff electrodes, which are self-biased to wrap around a nerve trunk in a spiral to provide close contact, has become an accepted method for nerve stimulation, as the structure of the electrode allows it to be installed around the nerve fiber without cutting or damaging the nerve. Another advantage of spiral nerve cuff electrodes lies in the fact that these electrodes require less stimulating current than other types of electrodes, and hence less charge injected into the tissue. In addition, cuff electrodes allow easy excitation of entire muscles rather than parts of muscles.

Various prior art cuff electrodes have been utilized in the past to apply electrical stimuli to nerves. U.S. Pat. No. 4,602,624 is directed to a cuff electrode which encircles a nerve trunk with at least one electrical energy conductive member held against the tissue and a non-conductive sleeve extending to either side of the conductive member. This cuff is a self-curling sheet which is biased to curl into a tight overlapping cylindrical spiral around the nerve trunk. U.S. Pat. No. 5,324,322 is directed to a nerve cuff electrode having a spiral cuff portion which is connected to a spiral lead portion. The spiral cuff portion is coiled around a nerve, while the spiral lead portion used to couple the device to an appropriate power source. U.S. Pat. No. 5,505,201 is directed to a helical nerve cuff electrode which curls into a helical spiral around a nerve fiber as it is ejected from a carrier tool.

Although these spiral cuff electrodes have proven effective, they do have drawbacks. As these electrodes are very delicate in construction, with very small and fragile wires and connections, the installation of cuff electrodes requires a very sensitive and exacting surgery. When these electrodes are to be installed in hard-to-reach areas of the body, it is often very difficult to implant them satisfactorily. The instrument used to install these electrodes must be rigid in construction to be able to carry and place the electrodes, yet flexible in order to maneuver the electrodes into the proper position in minimally accessible areas. In addition, the tool must be able to maintain the electrode in a flat uncurled position until ready for implantation, while it may be necessary to control the implantation of the electrode from a position remote from the implantation site.

The present invention provides a novel tool for implanting spiral nerve cuff electrodes which overcomes the above referenced problems and provides other advantages for the procedure.

SUMMARY OF THE INVENTION

It is therefore an object of the present invention to provide a tool for implanting spiral cuff electrodes by which the electrodes can be easily maneuvered into position in difficult-to-access areas within the body.

It is also an object of the present invention to provide a device which can accurately place a spiral nerve cuff electrode in its proper position by controlling the operation from a site remote from the electrode.

It is a further object of the present invention to provide a device for implanting cuff electrodes which is simple, easy to manufacture, and uncomplicated to operate.

These and other objects of the present invention are accomplished by a novel tool for carrying a spiral cuff electrode having a body, a control device mounted for rotation within the body, a valve carrying the electrode which is held by a vacuum, such that the valve is controllable to sequentially release the electrode to encircle a nerve.

BRIEF DESCRIPTION OF THE DRAWINGS

FIG. 1 is a left side elevational view of the instrument of the present invention;

FIG. 2 is a left side view, partly in phantom, of the body of the instrument of the present invention;

FIG. 3A is a left side view, partly in phantom, of the control device of the present invention;

FIG. 3B is a top view of the control device of FIG. 3A;

FIG. 4 is a side view, partly in phantom, of the end cap of the present invention;

FIG. 5 is a left side view, partly in phantom, of the rotatable valve section of the present invention;

FIG. 6 is an end view, partly in phantom, of the central valve section of the present invention;

FIG. 7 is a top view, partly in phantom, of the valve section of FIG. 6;

FIG. 8 is a side view, partly in phantom, of the valve section of FIG. 6;

FIG. 9 is a side view, partly in phantom, of the carrier valve section of the present invention.

FIG. 10 is an end view of the valve section shown in FIG. 9;

FIG. 11 is a side view, partly in phantom, of the connector of the present invention;

FIG. 12 is an end view of the carrier valve assembly of the present invention showing a cuff electrode in position for implantation;

FIG. 13 is a view similar to FIG. 12 showing the sequence of operation of the carrier valve assembly of the present invention.

FIG. 14 is an end view of the carrier valve assembly of the present invention showing a cuff electrode in the implanted position.

DETAILED DESCRIPTION OF THE PREFERRED EMBODIMENT

Referring more particularly to the drawings, there is shown in FIG. 1 an instrument, generally indicated at 10, which embodies the principles of the present invention. Instrument 10 contains a handle or body 12, an end cap 14, an electrode carrier valve assembly generally indicated at 16, a control device 18, a flexible tube 20 connecting carrier valve assembly 16 and control device 18, and a wire 22 located within flexible tube 20.

FIGS. 2–4 more clearly illustrate the body 12, end cap 14, and control device 18 of instrument 10 in greater detail. Body 12 consists of a hollow tubular section having a proximal edge 12a and a distal edge 12b, and containing an opening 24 through one side of body 12. Control device 18 includes a hollow tubular section 26 having an internal passageway 26a which is sized such that it may be rotatably accommodated within body 12. Control device 18 also includes a conical section 28 located at the distal end of tubular section 26, with section 28 having a distal end 28a of larger diameter than section 26 of control device 18 and that of body 12. The distal end 28b of conical section 28 contains a through hole 30 providing an opening to the interior of tubular section 26 of device 18. Finally, the proximal end of section 26 contains an internally threaded section 32, while the distal area of section 26 includes a cutout section 34.

End cap 14 includes an externally threaded distal section 36, a central section 38, and an internally threaded proximal section 40. Threadedly affixed to cap 14 at threaded section 40 is a connector fitting 42 which is coupled to a vacuum hose 44 (FIG. 1), which in turn is connected to a suitable vacuum source 46. Cap 14 also contains a passageway 48 which extends through sections 36, 38, and 40.

Referring now to FIGS. 5–9, carrier valve assembly 16 can be explained in greater detail. Assembly 16 includes a first rotatable valve section 50, a second central valve section 52, and a third carrier valve section 54. First valve section 50 includes a proximal tubular section 56, a circular flange 58, and a distal tubular section 60, along with a bore 62 which extends completely through valve section 50. Section 60 further includes an externally threaded portion 64 adjacent flange 58, a pair of grooves 66a and 66b which extend through section 60 to bore 62, and a through hole 68 which also extends through section 60 to bore 62.

Valve section 52 consists of a housing 70 with an outer wall 70a and having a flat rear surface 70b and an inner valve surface 70c. Housing 70 contains an open interior area 72 and also an internally threaded portion 74. Rear surface 70b contains an aperture 76 through its central region, while surface 70C has a series of three small ports 78a, 78b, 78c which connect the interior area 72 of housing 70 to the exterior of surface 70c. Finally, a pair of mortises 80a, 80b extend along the outer edge of valve section 52.

Carrier valve section 54 consists of a housing 90 having a flat surface 92 35 and a bottom edge 94 located essentially perpendicular to surface 92. A pair of tenons 96a, 96b which correspond to mortises 80a, 80b are located along each outer edge of surface 92. The interior surface of carrier valve 54 includes a flat surface 98, which is essentially parallel with bottom edge 94, a curved surface 100 terminating in a small recessed channel 102, and an angular surface 104. An upper surface 106 connects surface 104 to tenon 96a.

Surface 92 is more clearly seen in FIG. 10. Referring now to FIG. 10, surface 92 contains a series of aligned ports 110 which are located within a channel 112. A second series of aligned ports 114 are located within a channel 116, while a third series of ports 118 are located within a channel 120. Channel 120 contains an upwardly extending branch 120a. Ports 110 extend through carrier valve 54 and terminate in a linear array along angular surface 104. Ports 114 also extend through carrier valve 54 and terminate in a linear array along curved surface 100, while ports 118 extend through carrier valve 54 and terminate in a linear array along flat surface 98.

The assembly of instrument 10 can now be explained. A connector 122 (FIG. 11) includes a threaded bore 122a, a through hole 122b, and a second threaded bore 122c which connects the interior of hole 122b to the outer surface of connector 122. One end of wire 22 is inserted into hole 122b and fixed in position by use of appropriate attachment means, such as a set screw (not shown), threaded into bore 122c to hold wire 22 tightly within hole 122b. Connector 122 is then fixed in position within the interior of body 12 by use of appropriate attachment means, such as a screw (not shown) inserted through opening 24 through body 12 and threaded into bore 122a. The other end of wire 22 extends through hole 30 of device 18, which has been inserted into body 12 such that proximal end 28a of conical section 28 of device 18 abuts distal edge 12b of body 12. Distal section 36 of end cap 14 is threaded into section 32 of section 26 such that central section 38 of cap 14 abuts edge 12a of body 12. Connector 42, which is threadedly affixed to end cap 12, is coupled to vacuum source 46 via hose 44.

The end of wire 22 which extends from device 18 passes through flexible tube 20, bore 62 of valve section 50, and into aperture 76 within bottom surface 70b, where wire 22 is rigidly affixed by suitable means, such as welding, soldering, or other similar processes.

The construction of carrier valve assembly 16 can now be described in detail. Tubular section 60 of valve section 50 is contained within interior area 72 of valve section 52 and rotatably affixed by the threaded engagement of portions 64 and 74, such that flange 58 of section 50 abuts housing 70 of section 52. Flexible tube 20, which contains wire 22, is attached between end 28b of control device 18 and section 56 of valve section 50 by virtue of an interference fit of tube 20 with end 28b and section 56. Finally, carrier valve section 54 is slidably attached to valve section 52 by virtue of a dovetail joint formed by the interaction of mortises 80a, 80b with tenons 96a, 96b, which provides for precise positioning of valve sections 52 and 54.

Having described the elements of the tool of the present invention, the operation of the preferred embodiment of instrument 10 will now be described. Referring now to FIGS. 12, 13 and 14, a spiral nerve cuff electrode 130 having end sections 130a, 130b and a central section 130c is shown in position within carrier valve assembly 16 of tool 10. With vacuum source 46 attached to tool 10 via hose 44 and with tool 10 in its initial operating position, vacuum source 46 creates a suction at ports 110, 114, 118 of carrier valve section 54 via area 72, bore 62, tube 20, section 26, end cap 14, connector fitting 42, and hose 44, causing electrode 130 to be held in an uncoiled position against surfaces 98, 100, and 104 of valve section 54, while lead 132 of electrode 130 is accommodated within recessed channel 102. A selected nerve 134 can now be positioned relative to electrode 130 for installation.

When instrument 10 is positioned relative to nerve 134 as shown in FIG. 12, electrode 130 can now be released to encircle the nerve. By rotating end cap 14 slightly, control device 18 also rotates in response to this movement, as cap 14 and device 18 are coupled together by virtue of the threaded engagement of sections 32 and 36. In addition, valve section 50 rotates in response to the movement of end cap 14, as conical section 28 of device 18 is directly coupled to carrier valve assembly 16 by flexible tube 20. The fact that tube 20 is composed of a flexible material, such a plastic or polyethylene, allows valve section 50 to be rotated by end cap 14 when body 12 is situated in an angular relationship to carrier valve assembly 16. As control device 18 is rotatably mounted within body 12, and body 12 is rigidly coupled to central valve section 52 by virtue of wire 22 being affixed by connector 120 within body 12 and affixed within aperture 76 of valve section 52, carrier valve assembly 16 and body 12 of instrument 10 can be held in a particular static position while cuff electrode 130 is released around nerve 134 by the rotation of end cap 14.

The release of electrode 130 can be seen in sequence in FIG. 13. As end cap 14 is initially rotated, valve section 50 turns such that hole 68 is no longer in communication with port 78a of valve section 52, and consequently channel 112 and ports 110 of carrier valve section 54. Therefore, as the suction is removed from electrode 130 at section 104 of valve section 54, end section 130a curls around nerve 134, as shown at A in FIG. 13.

As end cap 14 is turned further, groove 66a rotates until it is no longer in communication with port 78b of valve section 52, and consequently channel 120 and ports 118 of carrier valve section 54. Thus, as the suction is released from electrode 130 at section 98 of valve section 54, end section 130b begin to curl toward nerve 134, as shown at B in FIG. 13.

Finally, as end cap 14 continues to rotate, groove 66b moves to a position out of communication with port 78c of valve section 52 and channel 116 and ports 114 of carrier valve section 54, releasing the suction at section 100 of valve section 54 on central region 130c of electrode 130 and allowing electrode 130 to curl completely around nerve 134, as shown in FIG. 14. When electrode 134 has been completely released from carrier valve assembly 16, instrument 10 can be carefully removed from the implantation site.

The maneuverability of instrument 10 can be appreciated during the installation process of the electrode about a nerve. For example, if it is necessary to implant a cuff electrode about the optic nerve within the head of a patient, it is very difficult to perform this procedure as the insertion point through the skull must be kept as small as possible, and the implantation site is hard to access, making electrode implantation a delicate process. With the present invention, as the electrode is held in its uncoiled position on carrier valve assembly 16 by a vacuum, assembly 16 can be easily maneuvered to the desired position relative to body 12 by virtue of flexible tube 20. Tube 20, which can be designed at any length, can be bent to a specific angle, yet it is stiff enough with wire 22 enclosed within to maintain a given position during an implantation procedure, but is pliable enough to also be repetitively changed by the user. When the electrode is correctly positioned relative to the nerve, the electrode is released by sequentially removing the vacuum from the sections of carrier valve 54. The release is controlled at the distal end of instrument 10 by rotation of end cap 14, and such motion is exclusive of the position of body 12. In this manner, body 12 can be grasped firmly to insure accurate positioning of the electrode while end cap 14 is rotated to properly release the electrode about the desired nerve.

As used herein and in the claims, such words as "distal", "proximal", "top", "bottom", and the like are used in conjunction with the drawings for purposes of clarity. It will be appreciated that instrument 10, in use, may be held in any appropriate orientation.

While the invention has been show and described in terms of a preferred embodiment, it will be understood that this invention is not limited to this particular embodiment and that may changes and modifications may be made without departing from the true spirit and scope of the invention as defined in the appended claims.

What is claimed is:

1. A tool for carrying an electrode for implantation about a nerve within a mammal comprising:
   a body;
   a control device, mounted for rotation with respect to said body;
   valve means, coupled to said control device and said body, having a plurality of ports which may be selectively controlled by said control device for releasably holding the electrode;
   a flexible tubing coupling said control device to said valve means;
   a wire rigidly coupling said body to said valve means;
   and vacuum means coupled to said valve means, for holding the electrode at said valve means;
   with said valve means further comprising a first valve section for releasably holding the electrode, a second valve section, rigidly affixed to said first valve section, rigidly coupling said valve means to said wire, and a third valve section, rotatably coupled to said second valve section, affixing said valve means to said flexible tubing such that said control device and said third valve section are coupled for rotation;
   whereby when said control device is rotated relative to said body, said valve means gradually releases the electrode such that the electrode can be coiled around a nerve within a mammal.

2. The tool of claim 1, wherein said body consists of a hollow cylinder, and said control device is located within said body.

3. The tool of claim 1, wherein said wire is positioned within said flexible tubing.

4. The tool of claim 1, wherein said first valve section includes at least one first port for contacting a portion of an electrode, at least one second port for contacting a portion of an electrode, and at least one third port for contacting a portion of an electrode.

5. The tool of claim 4, wherein said second valve section includes a first port for communicating with the at least one first port contained in said first valve section, a second port for communicating with the at least one second port contained in said first valve section, a third port for communicating with the at least one third port contained in said first valve section.

6. The tool of claim 5, wherein said third valve section includes a first opening for communicating with the first port contained in said second valve section, a second opening for communicating with the second port contained in said second valve section, and a third opening for communicating with the third port contained in said second valve section.

7. The tool of claim 6, wherein when said control device is at its initial position relative to said valve means, said vacuum means communicates with the at least one first, second, and third ports of said first valve section of said valve means to hold an electrode against said first valve section.

8. The tool of claim 7, wherein when said control device is rotated to a first position away from said initial position, shifting said first opening of said third valve section out of communication with said first port of said second valve section, said at least one first port of said first valve section is blocked from communication with said vacuum means, thereby releasing the portion of the electrode contacting said at least one first port of said first valve section.

9. The tool of claim 8, wherein when said control device is rotated to a second position, shifting said second opening of said third valve section out of communication with said second port of said second valve section, said at least one second port of said first valve section is blocked from communication with said vacuum means, thereby releasing the portion of the electrode contacting said at least one second port of said first valve section.

10. The tool of claim 9, wherein when said control device is rotated to a third position, shifting said third opening of said third valve section out of communication with said third port of said second valve section, said at least one third port of said first valve section is blocked from communication with said vacuum means, thereby releasing the portion of the electrode contacting said at least one third port of said first valve section.

11. The tool of claim 10, wherein when said control device is at said third position, said at least one first port, said at least one second port, and said at least one third port of said first valve section are all blocked from communication with said vacuum means.

12. The tool of claim 9, wherein when said control device is at said second position, said at least one second port and said at least one first port of said first valve section are blocked from communication with said vacuum means while said at least one third port of said first valve section remains in communication with said vacuum means.

13. The tool of claim 8, wherein when said control device is at said first position, said at least one first port of said first valve section is blocked from communication with said vacuum means while said at least one second port and said at least one third port of said first valve section remain in communication with said vacuum means.

14. A tool for use in implanting a spiral cuff electrode about a nerve, comprising:

a handle;

a control device, mounted for rotation within said body;

a valve assembly, comprising a first valve section containing a plurality of first ports for releasably holding a spiral cuff electrode in an uncoiled position, a second valve section, rigidly affixed to said first valve section, containing a plurality of second ports which communicate with said first ports within said first valve section, and a third valve section, rotatably coupled to said section valve section, having a plurality of third ports which communicate with said second ports within said second valve section;

a flexible tube affixing said control device to said third valve section such that said control device and said third valve section are coupled for rotation;

a wire located within said tube, rigidly coupling said handle to said second valve means;

and vacuum means, acting within said handle, control device, tube and valve assembly, for releasably holding a spiral cuff electrode against said first valve section;

such that when said control device is rotated, vacuum means is removed from said valve assembly, thereby releasing the spiral cuff electrode from said first valve section about a nerve.

15. A device for positioning an object, comprising:

a handle to aid in positioning the device;

means for controlling operation of the device;

valve means, located distally from said handle and operatively connected to said control means, having a plurality of ports which may be selectively controlled by said control means for releasably holding the object;

vacuum means, coupled to said valve means, for holding the object against said valve means by suction force;

and a plurality of flexible tubes, coupling said vacuum means and said control means to said valve means, with said valve means further comprising a first valve section for releasably holding the object, a second valve section, coupled to said first valve section, affixing said valve means to said handle, and a third valve section, coupled for rotation relative to said second valve section, affixing said valve means to one of said flexible tubes;

such that when said control means is activated, suction force is sequentially removed from said ports of said valve means, gradually releasing the object.

16. The device of claim 15, wherein said first valve section contains a plurality of ports, each of which is independently coupled to said vacuum means and capable of contacting a separate portion of the object held by said valve means, such that the suction force from said vacuum means can be selectively removed from each port.

* * * * *